US006967082B1

(12) United States Patent
Stenflo (10) Patent No.: US 6,967,082 B1
(45) Date of Patent: Nov. 22, 2005

(54) MONOCLONAL ANTIBODY

(75) Inventor: Johan Stenflo, Malmö (SE)

(73) Assignee: Forskarpatent I Syd AB, Lund (SE)

( * ) Notice: Subject to any disclaimer, the term of this patent is extended or adjusted under 35 U.S.C. 154(b) by 0 days.

(21) Appl. No.: 09/890,949

(22) PCT Filed: Feb. 3, 2000

(86) PCT No.: PCT/SE00/00210

§ 371 (c)(1),
(2), (4) Date: Sep. 10, 2001

(87) PCT Pub. No.: WO00/47626

PCT Pub. Date: Aug. 17, 2000

(30) Foreign Application Priority Data

Feb. 9, 1999 (SE) .................................. 9900431

(51) Int. Cl.[7] ............................................. G01N 33/55
(52) U.S. Cl. ................... 435/7.92; 435/7.93; 435/9.94; 435/345; 436/514; 436/15; 436/547
(58) Field of Search .............................. 435/7.92, 7.93, 435/9.94, 345; 436/514, 15, 547

(56) References Cited

U.S. PATENT DOCUMENTS 5,834,290 A * 11/1998 Egelrud et al. ............. 435/226

FOREIGN PATENT DOCUMENTS

JP            2-236452      9/1990
WO     WO 98/22509 A1     5/1998

OTHER PUBLICATIONS

Gaussem P et al. Journal of Biological Chemistry 1993 268: 12150-12155.*
Poller et al. Journal of Biological Chemistry 1995 270: 2841-2845.*
Kenneth A. Bauer et al., "Detection of Protein C Activation in Humans," *J. Clinical Invest. The American Society for Clinical Investigation, Inc.*, vol. 74 (1984) pp. 2033-2041.
András Gruber et al., "Direct Detection of Activated Protein C in Blood From Human Subjects," *Blood*, vol. 79, No. 9 (1992) pp. 2340-2348.
Francisco España et al., "Quantification of Circulating Activated Protein C in Human Plasma by Immunoassays—Enzyme Levels are Proportional to Total Protein C Levels," Thrombosis and Haemostasis—F.K. Schattauer Verlagsgesellschaft mbH (Stuttgart) 75 (1) (1996) pp. 56-61.
Francisco España et al. "Determination of Functional and Antigenic Protein C Inhibitor and Its Complexes with Activated Protein C in Plasma by Elisa's," *Thrombosis Research*, vol. 55 (1989) pp. 671-682.

Francisco España et al. "Determination of Plasma Protein C Inhibitor and of Two Activated Protein C-Inhibitor Complexes in Normals and in Patients with Intravascular Coagulation and Thrombotic Disease," *Thrombosis Research* vol. 59 (1990) pp. 593-608.
Kouzou Minamikawa et al. "Increased Activated Protein C-Protein C Inhibitor Complex Levels in Patients with Pulmonary Embolism," *Thrombosis and Haemostasis*- F.K. Schattauer Verlagsgesellschaft mbH (Stuttgart) 71 (2) (1994) pp. 192-194.
Martin Laurell et al., "Monoclonal Antibodies Against the Heparin-Dependent Protein C Inhibitor Suitable for Inhibitor Purification and Assay of Inhibitor Complexes," Thrombosis and Haemostasis—F.K. Schattauer Verlagsgesellschaft mbH (Stuttgart) 60 (2) (1988) pp. 334-339.
Ariane de Agostini et al., "A Common Neoepitope is Created When the Reactive Center of C1-Inhibitor is Cleaved by Plasma Kallikrein, Activated Factor XII Fragment, C1 Esterase, or Neutriphil Elastase," *J. Clin. Invest*, vol. 82 (1988) pp. 700-705.
Shinji Asakura et al., "A Monoclonal Antibody That Triggers Deacylation of an Intermediate Thrombin-Antithrombin III Complex," *The Journal of Biological Chemistry*, vol. 264, No. 23, (1989) pp. 13736-13739.
Ingemar Björk et al., "Immunologic Evidence for Insertion of the Reactive-Bond Loop of Antithrombin into the A β-Sheet of the Inhibitor During Trapping of Target Proteinases," Biochemistry, vol. 32, (1993) pp. 6501-6505.
Ann-Kristin Öhlin et al., "Calcium-Dependent Interaction Between the Epidermal Growth Factor Precursor-Like Region of Human Protein C and a Monoclonal Antibody," *The Journal of Biological Chemistry*, vol. 262, No. 28, (1987) pp. 13798-13804.

(Continued)

*Primary Examiner*—Long V. Le
*Assistant Examiner*—Jacob Cheu
(74) *Attorney, Agent, or Firm*—Buchanan Ingersoll PC (57) ABSTRACT

The present invention relates to a monoclonal antibody suitable for monitoring the activity of systems involving protein C inhibitor, a method for preparation of the monoclonal antibody, a method for monitoring the activity of systems involving protein C inhibitor and a method for diagnosis of e.g. venous thrombosis, wherein the monoclonal antibody is utilized. The monoclonal antibody is suitable for monitoring the activity of systems involving protein C inhibitor, and it has specific affinity for both i) a complex between a serine proteinase and an inhibitor thereof, and ii) a cleaved and uncomplexed form of the inhibitor, but has substantially no specific affinity for the inhibitor in its uncleaved and uncomplexed form; or a derivative thereof having the same biological activity.

20 Claims, 4 Drawing Sheets

OTHER PUBLICATIONS

Carl A.K. Borrebaeck et al., "Production and Characterization of a Monoclonal Antibody Against the Seed Lectin of the *Dolichos biflorus* Plant," *The Journal of Biological Chemistry,* vol. 256, No. 10, (1981) pp. 4723-4725.

Martin Laurell et al., "Protein C Inhibitor in Human Body Fluids," *The American Society for Clinical Investigation, Inc.* vol. 89, (1992) pp. 1094-1101.

Xuhua He et al., "Binding Site for C4b-Binding Protein in Vitamin K-Dependent Protein S Fully Contained in Carboxy-Terminal Laminin-G-type Repeats. A Study Using Recombinant Factor IX-Protein S Chimeras and Surface Plasmon Resonance," *Biochemistry* vol. 36, No. 12, (1997) pp. 3745-3754.

Suzuki, Koji et al., "Characterization of a cDNA for Human Protein C Inhibitor", *The Journal of Biological Chemistry,* Apr. 24, 1986, vol. 262, No. 2, The American Society of Biological Chemists, Inc., Bethesda, MD.

Gettins, Peter G. W., "Serpin Structure, Mechanism, and Function", *Chemical Reviews*, vol. 102, No. 12, pp. 4751-4803, Department of Biochemistry & Molecular Genetics, Chicago, IL.

Huntington, James et al., "Crystal Structure of Protein C Inhibitor Provides Insights into Hormone Binding and Heparin Activation", *Structure,* Feb., 2003, vol. 11, pp. 205-215, Elsevier Science, Ltd., Cambridge, MA.

* cited by examiner

MONOCLONAL ANTIBODY

FIELD OF THE INVENTION

The present invention relates to a monoclonal antibody suitable for monitoring the activity of systems involving protein C inhibitor, a method for preparation of said monoclonal antibody, a method for monitoring the activity of systems involving protein C inhibitor and a method for diagnosis of e.g. venous thrombosis, wherein said monoclonal antibody is utilised.

BACKGROUND OF THE INVENTION

Protein C is a proenzyme to "activated protein C". Activated protein C, hereinafter denoted APC, is a serine proteinase, and its proenzyme protein C is a liversynthesised glycoprotein having 461 amino acid residues and a molecular weight of approximately 62 kDa. Protein C carries two parts denoted the light and the heavy chain, respectively (formed by limited proteolysis of a single chain precursor). The light chain is glycosylated on its Asn 97 residue, whereas the heavy chain is glycosylated on its Asn 248, Asn 313 and Asn 329 residues (Asn 329 being glycosylated only in so-called "single chain protein C"). Of all the protein C in plasma, about 85% contains both the light and heavy chain, whereas about 15% consists of single chain protein C. There is no known difference in biological activity between these two forms of protein C.

The light chain of protein C contains an amino-terminal domain with nine γ-carboxyglutamic acid (Gla) residues, which have been formed by vitamin K-dependent carboxylations. This domain is followed by two domains, both of which are homologous to the epidermal growth factor (EGF) precursor. Of said two domains, one has a single hydroxylated aspartic acid residue, i.e. consists of erythro-β-hydroxyaspartic acid. The light and the heavy chains are linked together via one disulfide bond only.

Moreover, protein C requires vitamin K for its normal biosynthesis, and it circulates in blood plasma at a concentration of approximately 4 mg/l.

Protein C is an important regulator of blood coagulation, and it is activated by thrombin complexed with thrombomodulin. This activation involves removal of an activation peptide with 12 amino acids from the amino-terminal end of the heavy chain of protein C, whereby APC is formed. APC is a typical serine proteinase with high arginyl bond specificity.

The substrates degraded by APC are the cofactors known as factor V/$V_a$ and factor VIII/$VIII_a$, respectively, where "$_a$" denotes the active form of the cofactor. In coagulation pathways, the factor $VIII_a$ forms a membrane-bound complex with the factor $IX_a$, whereby the coagulation factor X is activated to a serine proteinase denoted coagulation factor $X_a$. Furthermore, the factor $V_a$ forms a membrane-bound complex with the coagulation factor $X_a$, whereby prothrombin is activated to thrombin.

The degradation of the factors $V_a$ and $VIII_a$ by APC requires two cofactors. These are protein S, which is a vitamin K-dependent protein, and factor V, which is the unactivated form of factor $V_a$. The degradation results in cleavage of the factors $V_a$ and $VIII_a$, whereby their affinity for factors $X_a$ and $IX_a$, respectively, is reduced. Thus, said cleavage results in a reduction of the rate of formation of both thrombin and coagulation factor $X_a$. In other words, the blood coagulation cascade is turned off.

As other serine proteinases, APC has its inhibitors. These are protein C inhibitor (hereinafter denoted PCI; plasma concentration approximately 4 mg/l), $\alpha_1$-proteinase inhibitor (hereinafter denoted $\alpha_1$-antitrypsin; plasma concentration approximately 1 g/l) and $\alpha_2$-macroglobulin (plasma concentration approximately 2 g/l). PCI and $\alpha_1$-antitrypsin belong to a group of inhibitors sometimes referred to as serpines (serine proteinase inhibitors), and form 1:1 complexes with APC.

The complex formation between APC and PCI proceeds at a slow rate, and it proceeds even slower in respect of $\alpha_1$-antitrypsin. This slow rate is manifested by a long half-life for APC in plasma, wherein $t_{1/2}$ is about 20 min. However, the rate of complex formation between APC and PCI is increased by heparin.

Upon complex formation with APC, the serpin is cleaved in its so-called bait region, whereby a stable intermediate acyl complex is formed. With time, the intermediate acyl complex dissociates, whereby APC is regenerated and a proteolytically modified, i.e. cleaved, inactive serine proteinase inhibitor is formed.

The intermediate acyl complexes are removed rather rapidly from the circulatory system. $T_{1/2}$ in baboons is approximately 40 and 140 min for the APC:PCI and APC:$\alpha_1$-antitrypsin complexes, respectively. PCI appears to be the prime inhibitor for APC with $\alpha_1$-antitrypsin and $\alpha_2$-macroglobulin taking over as the PCI concentration is substantially lowered.

PCI also inhibits thrombin and factor $X_a$, both of which are blood coagulation proteinases. In addition, PCI inhibits trypsin, chymotrypsin, urokinase plasminogen activator (uPA), tissue type plasminogen activator (tPA), plasma kallikrein, factor $XI_a$, prostatic specific antigen (PSA) and the prostata specific kallikrein-like serine proteinase denoted HGK1.

The biological importance of APC can be illustrated in several ways, e.g.

i) newborn children with homozygous protein C deficiency die during the first days of life in a clinical condition denoted *Purpura fulminans*, which is the result of widespread thrombotisation of capillaries;

ii) heterozygosity for protein C deficiency has in many cases been associated with a thrombofilia that accounts for approximately 2% of all hereditary thrombofilia;

iii) a frequently occurring (present in 2–10% of Caucasian populations) point mutation in factor V, rendering factor V/$V_a$ resistant to degradation by APC, is associated with a mild form of hereditary thrombofilia in the heterozygous form and a more severe form of thrombofilia in the homozygous form;

iv) disseminated intravascular coagulation is associated with a depletion of activated protein C, a process which often leads to a fatal outcome;

v) gram negative septicemial (caused by e.g. meningococci) leads to a depletion of activated protein C, a condition shown to be fatal in baboons as well as in humans.

In summary, the considerable biological importance of serine proteinases, particularly protein C, as regulators of blood coagulation as well as their role as key proteins in the so-called protein C anticoagulant pathway has resulted in a great need in the art to develop powerful research tools and extract clinically relevant information from e.g. the concentration of APC in plasma.

In particular, such clinically relevant information could be very useful in the diagnosis of e.g. venous or arterial thrombosis, including coronary infarction or pulmonary embolism.

Prior Art

To serve the above-mentioned purposes and measure the activation of anticoagulant systems involving protein C, numerous methods have been developed, as set forth below.

In Bauer, K. A., Kass, B. L., Beeler, D. L., Rosenberg, R. D., *J. Clin. Invest.*, 74:2033–2041 (1984), a method is disclosed, wherein the plasma concentration of the activation peptide removed from protein C (vide supra) is measured. Since said activation peptide has a very high renal clearance, its plasma concentration is low. Thus, this method is cumbersome as it requires large amounts of plasma.

In Gruber, A., Griffin, J. H., *Blood*, 79:2340–2348 (1992), a method is disclosed, wherein the plasma concentration of APC is measured. Here, an ELISA technique with a catching monoclonal antibody against protein C was used. Since said catching monoclonal antibody does not inhibit the activity of APC, an amidolytic assay was used. However, due to the low plasma concentration of APC, the incubation time was generally very long (up to days) and impractical.

In an approach disclosed in Espana, F., Zuazu, I., Vicente, V., Estelles, A., Marco, P., Aznar, J., *Thromb. Haemost.*, 75:56–61 (1996), heparin-mediated enhancement of the rate of complex formation between APC and PCI is utilised. This method requires the presence of e.g. heparin, benzamidine and D-phenylalanyl-L-prolyl-L-arginine chloromethyl ketone (PPAC).

However, the most relevant approaches disclosed relate to methods, wherein the concentration of a complex between APC and PCI, or between APC and $\alpha_1$-antitrypsin, is measured by use of monoclonal antibodies. These approaches are all based on the assumption that said concentration reflects the concentration of APC, and hence also the degree of activation of the protein C anticoagulant system. Here, a catching monoclonal antibody raised against either APC or PCI is used together with a suitable tracer agent in an ELISA technique.

Thus, if the catching monoclonal antibody is specific for PCI, the tracer agent could be an antibody specific for an epitope in protein C, or vice versa. However, an inherent problem in this approach is that the concentration of free, uncomplexed PCI and APC, respectively, is very high in comparison with the APC:PCI complex to be measured. As an example, due to competitive binding between free, uncomplexed PCI and complex-bound PCI to a catching monoclonal antibody raised against PCI, the sensitivity of such an approach is greatly reduced. Typical such approaches are disclosed in JP 02-236 452, Espana, F., Griffin, J. H., *Thromb. Res.*, 55:671–682 (1989) and Espana, F., Vicente, V., Scharrer, I., Tabernero, D., Griffin, J. H., *Thromb. Res.*, 59:593–608 (1990).

In an approach disclosed in Minamikawa, K., Wada, H., Wakita, Y., Ohiwa, M., Tanigawa, M., Deguchi, K., Hiraoka, N., Huzioka, H., Nishioka, J., Hayashi, T., *Thromb. Haemost.*, 71:192–194 (1994), a precipitated barium salt is used to bind PCI in complex with APC, whereas uncomplexed PCI does not bind to the precipitated barium salt. After centrifugation and dissolution in EDTA (aq), the sample is subjected to ELISA, wherein a catching monoclonal antibody raised against PCI is used. Although useful from a sensitivity point of view, this approach is time-consuming as well as laborious.

In Laurell, L., Carlson, T. H., Stenflo, J., *Thromb. Haemost.*, 60:334–339 (1988), it is disclosed monoclonal antibodies raised against cleaved PCI, wherein said monoclonal antibodies are applied in an assay for measuring the plasma concentration of APC:PCI complexes. All of said monoclonal antibodies also had specific affinity for uncleaved, uncomplexed PCI.

In WO 9822509, there is disclosed monoclonal antibodies which bind specifically to the PSA-ACT complex without significant cross-reactivity with PSA, ACT or CG-ACT. These antibodies are not suitable for monitoring the activity of systems involving protein C inhibitor.

In summary, there is still a great need in the art for a monoclonal antibody with high specific affinity for a serine proteinase inhibitor, e.g. PCI, in complex with a serine proteinase, e.g. APC, where said monoclonal antibody has substantially no affinity for PCI in its uncomplexed form.

DISCLOSURE OF THE INVENTION

According to the invention, there is now provided a new monoclonal antibody which overcomes the problems in the art referred to above. The monoclonal antibody according to the invention is suitable for monitoring the activity of systems involving protein C inhibitor, such as anticoagulant systems, and said monoclonal antibody is characterised by having specific affinity for both i) a complex between a serine proteinase and an inhibitor thereof, and ii) a cleaved and uncomplexed form of said inhibitor, while having substantially no specific affinity for said inhibitor in its uncleaved and uncomplexed form; or being a derivative thereof having the same biological activity.

The monoclonal antibody according to the present invention is obtainable by immunisation of an animal with a mixture of i) a complex between a serine proteinase and an inhibitor thereof, and ii) a cleaved form of said inhibitor, followed by screening for and isolation of said monoclonal antibody. Said animal is preferably a mouse, most preferably a Balb/c mouse.

Preferably, said serine proteinase is selected from the group consisting of activated protein C (APC), thrombin, coagulation factor $X_a$, trypsin, chymotrypsin, urokinase plasminogen activator (uPA), tissue type plasminogen activator (tPA), plasma kallikrein, factor $XI_a$, HGK1 and prostatic specific antigen (PSA).

As said inhibitor, either protein C inhibitor (PCI) or $\alpha_1$-antitrypsin is preferred.

In the most preferred embodiment, the monoclonal antibody according to the invention is obtainable, or obtained, by immunisation with a mixture of cleaved PCI and PCI in complex with PSA.

In another aspect, the present invention also relates to a method for preparation of a monoclonal antibody as defined above, wherein an animal is immunised with a mixture of i) a complex between a serine proteinase and an inhibitor thereof, and ii) a cleaved and uncomplexed form of said inhibitor, followed by screening for and isolation of said monoclonal antibody.

In yet another aspect, the present invention relates to a method for monitoring the activity of anticoagulant systems involving protein C, wherein a monoclonal antibody as defined above is used in an immunoassay.

Preferably, said immunoassay comprises a sandwich-type immunoassay. More preferably, said sandwich-type immunoassay is a DELPHIA®, ELISA or magnetic bead technique comprising a tracer agent and said monoclonal antibody bound to a surface.

In an embodiment of said method, said tracer agent comprises an antibody having specific affinity for said serine proteinase or an epitope shared by said serine proteinase and said inhibitor.

In another embodiment, said tracer agent is conjugated to a suitable enzyme and/or labelled with a tracing substance. Said enzyme is e.g. an alkaline phosphatase, horse radish peroxidase or a β-galactosidase. Said tracing substance is e.g. $^{125}I$, $^{131}I$, $Eu^{3+}$ or $Sm^{3+}$ or a similar lanthanide.

In a further aspect, the present invention also relates to a method for diagnosis of venous thrombosis, arterial thrombosis, embolism, coronary infarction, disseminated intravascular coagulation or disorders involving lupus anticoagulants, wherein a monoclonal antibody as defined above is utilised.

Furthermore, this invention relates to a method for diagnosis of venous thrombosis, arterial thrombosis, embolism, coronary infarction, disseminated intravascular coagulation or disorders involving lupus anticoagulants, wherein a monitoring method as defined above is utilised.

Moreover, the present invention relates to the use of a monoclonal antibody as defined above for in vitro diagnosis of venous thrombosis, arterial thrombosis, embolism, coronary infarction, disseminated intravascular coagulation or disorders involving lupus anticoagulants.

Also, this invention concerns the use of a monitoring method as defined above for in vitro diagnosis of venous thrombosis, arterial thrombosis, embolism, coronary infarction, disseminated intravascular coagulation or disorders involving lupus anticoagulants. In yet another aspect, the present invention relates to a kit for qualitative or quantitative determination of the activity of systems involving protein C inhibitor comprising a monoclonal antibody as defined above.

Thus, the present invention allows for precise quantitative measurements of complexes between e.g. human APC and PCI in blood plasma. Indeed, the present invention encompasses measurements of complexes between PCI and thrombin or any other serine proteinase known to form complexes with PCI, e.g. coagulation factor $X_a$ (this embodiment requires the exchange of the tracer agent only).

Some of the incentives for the use of a mixture of cleaved and complexed serine proteinase inhibitor for immunisation were gathered from mainly three sources. Firstly, it has been reported that certain monoclonal antibodies against the serpins antithrombin and C-1 esterase inhibitor (see e.g. de Agostini, A., Patston, P. A., Marottoli, V., Carrel, S., Harpel, P. C., Schapira, M., *J. Clin. Invest.*, 82:700–705 (1988) and Asakura, S., Matsuda, M., Yoshida, N., Terukina, S., Kihara, H., *J. Biol. Chem.*, 264:13736–13739 (1989)) are more or less selective for the complexed form of the inhibitor, albeit no such antibodies have been identified against PCI. Secondly, it has been disclosed in e.g. Björk, I., Nordling, K., Olson, S. T., *Biochemistry*, 32:6501–6505 (1993) that thrombin:antithrombin complexes and antithrombin cleaved from such complexes share epitopes. These epitopes are not present on native antithrombin. Thirdly, it has been reported by e.g. Espana, F. and Griffin, J. H. (vide supra) that human seminal plasma has a PCI concentration that is about 50-fold higher in comparison with its blood plasma concentration. However, the PCI present in human seminal plasma is unable to form complexes with APC. Indeed, the PCI present in human seminal plasma is the cleaved form of PCI.

The monoclonal antibody according to the present invention, when used as catching antibody in e.g. a sandwich assay, has very high specific affinity for PCI in complex with APC as well as for the proteolytically cleaved PCI, but has substantially no or very low specific affinity for native PCI, viz PCI in its uncleaved and uncomplexed form. In other words, the native PCI has no influence on the binding of APC:PCI complexes to a surface having the monoclonal antibody according to the present invention bound thereto. Thus, there is substantially no competitive binding of the native PCI to said surface, whereby the sensitivity of the method according to the invention is high.

The method according to the present invention has been devised such that it can easily be automated and adopted for use in modern automated laboratory instrumentation using e.g. magnetic beads coated with the monoclonal antibody of the invention.

The present invention is applicable both as a powerful research tool and in conjunction with diagnosis of e.g. venous thrombosis, embolism and coronary infarction. In particular, the latter application could be very useful as it may detect coronary infarction much earlier than existing methods, most of which measure the concentration of enzymes or other proteins released from the damaged myocardium (CK-MB, troponin T or myoglobin). The currently used methods are not diagnostically helpful until coronary ischemia has already damaged the myocardium. Detectable levels of CK-MB and troponin T are usually not present until 3–5 h (2–3 h for myoglobin) after the infarction, depending on its size.

Furthermore, the present invention may also help in the differentiation between coronary infarction and unstable angina, thereby improving current diagnostic procedures most significantly.

In a sandwich-type immunoassay, such as a DELPHIA@ technique, two monoclonal antibodies are used. According to a preferred embodiment of the present invention, one has specific affinity for PCI, and this monoclonal antibody is bound to a surface and denoted "catcher" in a DELPHIA@ context. The other monoclonal antibody has specific affinity against protein C and is denoted "tracer agent" in a DELPHIA® context. According to the present invention, the catcher has been carefully selected to circumvent the problems associated with the prior art (vide supra), i.e. that the large molar excess (normally more than 1000-fold) of uncomplexed protein, be it protein C or PCI, competes with the complexes to be measured by binding to a surface-bound monoclonal antibody.

Thus, in a preferred embodiment, the inventor has generated mouse monoclonal antibodies which have very high specific affinity for complexed PCI and cleaved PCI, but substantially no affinity for native PCI, viz PCI in its uncleaved and uncomplexed form. Such monoclonal antibodies are used as catcher in an immunoassay, as set forth below, and they were obtained by immunising Balb/c mice with a mixture of cleaved PCI and PCI in complex with a serine proteinase known as prostatic specific antigen (PSA). Furthermore, the inventor has devised approaches for carefully selecting, i.e. screening and isolating, such monoclonal antibodies, as is disclosed hereinbelow.

The present invention is further illustrated by the following non-limiting examples together with the accompanying figures.

DESCRIPTION OF THE FIGURES

FIG. 3 depicts dose-response curves for measurements of APC:PCI complexes. Each point represents the mean value of duplicate measurements. (♦) illustrates APC:PCI complexes in buffer, whereas (Δ) illustrates APC:PCI complexes in citrated plasma to which benzamidine has been added to a final concentration of 50 mM. The signal given by APC:PCI complexes prior to the addition of standard has been subtracted.

EXAMPLES

Preparation of Proteins:

Native PCI was purified from human plasma according to a method described in Laurell, M. et al. (vide supra) Cleaved PCI and PCI in complex with PSA were purified from human seminal plasma using the same method.

Protein C was purified from human plasma by adsorption to barium citrate, elution with EDTA, column chromatography on DEAE Sepharose® and use of an immobilised monoclonal antibody against protein C(HPC-4) that recognises a calcium-dependent epitope in the N-terminal EGF-like domain, as disclosed in Ohlin, A. K., Stenflo, J., *J. Biol. Chem.*, 262:13798–13804 (1987). Protein C was eluted from the column with 0,1 M sodium acetate/acetic acid buffer containing 0,5 M NaCl (pH 4,0). By addition of concentrated Tris buffer, an immediate adjustment to pH 7,5 was performed.

APC was prepared by thrombin-mediated activation of protein C, followed by isolation of APC by chromatography on an HPC-4 column, as described by Ohlin, A. K. and Stenflo, J. (vide supra).

Complexes used as standard in the method of measuring APC:PCI complexes were made by incubation of APC with a two-fold molar excess of PCI in 50 mM Tris-HCl, 0,1 M NaCl, 1 mM EDTA with pH 7,5. The complexes were isolated by affinity chromatography on an HPC-4 column, as described above. The purity of the isolated complex was established by SDS-PAGE and silver staining of the gel. The concentration of the complex in a standard solution was determined by measurement of Gla, assuming the presence of nine Gla residues per protein C molecule. Typically, the standard solution was made 0,1% in bovine serum albumin (BSA) and stored in aliquots at −70° C.

Used Methods:

In the DELPHIA® assay, microtiter plates (Fluor Maxisorp, Nunc) coated with the monoclonal antibody M52 (1 µg/100 µl per well) and incubated overnight at +4° C. were washed with a wash solution (Wallac) and blocked with 0,7% BSA in an assay buffer (Wallac) for 2 h. After washing of the plates, 100 µl of each fraction, with a dilution of 1:1000 in assay buffer, was added to the wells. The plates were incubated for 1 h on a DELPHIA@ plate shaker (Wallac) and then washed. Eu$^{3+}$ labelled monoclonal antibodies M11-5 (B and C in FIG. 1) or HPC-4 (A in FIG. 1), having a dilution in assay buffer to a concentration of 20 ng/100 µl, were added, followed by 1 h incubation on the shaker. After washing, 200 µl enhancement solution (Wallac) was added, followed by 5 min incubation on the shaker. Fluorescence was then recorded in a DELPHIA® fluorimeter (Wallac).

Surface plasmon resonance (SPR) was measured with the BIAcore® technology (Pharmacia). Streptavidin was immobilised on the BIAcore® sensorchip CM5 according to the instructions of the manufacturer. The immobilised streptavidin gave between 5400 and 6800 response units (RU). Biotinylated antibody, having a concentration of 0,34 mg/ml in 10 mM Tris-HCl/150 mM NaCl (pH 7,75), was immobilised at a flow rate of 5 µl/min, which resulted in a response of 2800–3000 RU. Aliquots of protein stock solution were diluted in flow buffer and 20 µl was injected during the association phase at a constant flow rate of 5 µl/min. The dissociation phase was monitored at the same flow rate for 10 min. The system was regenerated by short pulses of 50 mM NaOH at a flow rate of 2 µl/min. For the fitting of the lines to the experimental data, see e.g. He, X., Shen, L., Malmborg, A. C., Smith, K. J., Dahlback, B., Linse, S., *Biochemistry*, 36:3745–3754 (1997).

Production of Monoclonal Antibodies:

Balb/c mice were immunised with a mixture of PCI in complex with PSA (approximately 80%) and PCI cleaved from such a complex (approximately 20%). Each mouse was immunised three times with approximately 10 µg of said mixture each time. The two first immunisations were made intracutaneously with said mixture emulsified in Freund's complete adjuvant, whereas the third immunisation was administered subcutaneously with Freund's incomplete adjuvant. Testing of the mouse plasma, using an ELISA with an appropriate antigen coated in a 96 well microtiter plate, indicated a good antibody response after about two months. Five, four and three days prior to cell fusion, the mice were injected intraperitoneally with approximately 50 µg of the same immunogen (no adjuvant) each time. On cell fusion, the spleen cells were extracted and fused with the myeloma cell line SP2/—Ag14 using 45% polyethylene glycol 1540 and 7% DMSO (dimethyl sulphoxide) under standard conditions (see Borrebäck, C. A. K., Eylar, M. E., *J. Biol. Chem.*, 256:4723–4725 (1981)). Fused cells in DMEM medium supplemented with HAT (hypoxanthine, aminopterin, thymidine) were seeded into 96 well microtiter plates at a cell density of approximately 10$^5$ cells per well together with approximately 2×10$^4$ feeder cells per well. After about ten days, hybridoma supernatants were screened for antibody production.

Clones producing antibodies with interesting properties were identified as described below. The hybridomas were subcloned twice by limiting dilution using 96 well microtiter plates (0,5 to 1 cell per well) using mouse peritoneal macrophages as feeder cells. Stable clones producing monoclonal antibodies of interest were grown to high cell density and injected intraperitoneally into pristane-primed (0,2 ml per mouse) mice for antibody production. Antibodies were also produced on preparative scale by tissue culture (Technomouse®, Integra Biosciences). The antibody was purified from the ascitic fluid/tissue culture medium using chromatography on Protein A Sepharose® according to the instructions of the manufacturer. The cell lines were preserved frozen in 95% calf serum and 5% DMSO in liquid nitrogen.

Procedures for the identification of antibody producing clones that were specific for the complexed/-cleaved form of PCI were carefully tailored. Microtiter plates were coated overnight with rabbit antimouse immunoglobulins (DAKO; 1 μg/well in 50 μl) in 0,1 M carbonate buffer with pH 9,6. After washing, the wells were "blocked" for 15 min with a solution of bovine serum albumin (10 mg/ml, 100 μl per well) in 50 mM Tris-HCl, 0,1 M NaCl with pH 7,4. After washing, culture medium was added to identify antibody producing clones. After washing again, the wells were incubated with a tracer agent in the above buffer for 1 h. As $^{125}$I-labelled tracer agents, native PCI as well as APC:PCI complexes were used. The clones were also tested with the same method and found not to react with APC. After 1 h of incubation with the tracer agent, the plates were washed with the buffer, after which the radioactivity was measured. By having APC in the complex labelled with $^{125}$I, it was possible to select antibody producing clones that bound PCI in complex with APC. Moreover, a comparison with the binding of labelled, native PCI helped to identify clones that bound PCI in complex with APC with high specific affinity, but had a low specific affinity for native PCI.

One of the antibodies (M36) with specific affinity for APC:PCI complexes and cleaved PCI was carefully characterised. Three other monoclonal antibodies were also used; one against protein C that has been characterised (Ohlin, A. K. and Stenflo, J., vide supra), and two against PCI which do not discriminate between cleaved and native PCI. One of the latter two antibodies has been described before (M11-5; Laurell, M., Christensson, A., Abrahamsson, P- A., Stenflo, J., Lilja, H., J. Clin. Invest., 89:1094–1101 (1992)), whereas the other one (M52) was new (preparation disclosed herein).

Figure 1:
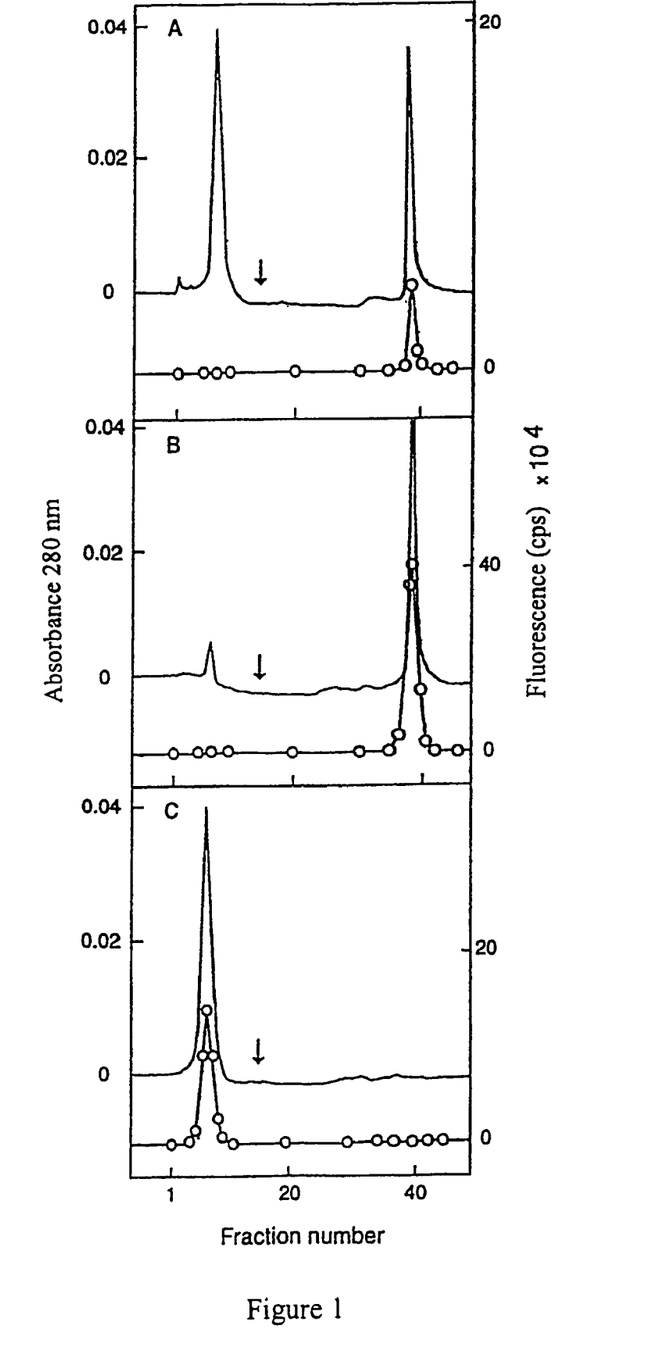
FIG. 1 shows affinity chromatograms for APC-complexed (A), cleaved (B) and native (C) PCI, respectively, obtained on an Affi Gel® 10 column (0,5×10 cm), onto which the monoclonal antibody M36 was immobilised. In each one of the samples A, B and C, 30 µg of the respective PCI analyte was chromatographed. The column was equilibrated with 50 mM Tris-HCl/0,5 M NaCl (pH 7,5). The flow rate was 0,1 ml/min. Bound protein was eluted with 0,1 M glycine-HCl/ 0,5 M NaCl with pH 2,7 (indicated by the arrow). The continuous line represents absorbance, whereas the "o—o"-line represents fluorescence. The early eluting peak in A consists of UV absorbing low molecular weight compounds and APC from cleaved complexes.

Characterisation of Monoclonal Antibodies:

Several monoclonal antibodies with the appropriate properties were produced. Of these, M36 was carefully characterised. This monoclonal antibody was immobilised on an Affi Gel® 10 column (Biorad) and APC-complexed (A), cleaved (B) and native (C) PCI were chromatographed on the column, as is shown in FIG. 1. The antibody bound to both cleaved and complexed PCI with high affinity, but was found not to bind or even retard the native PCI.

Figure 2A:
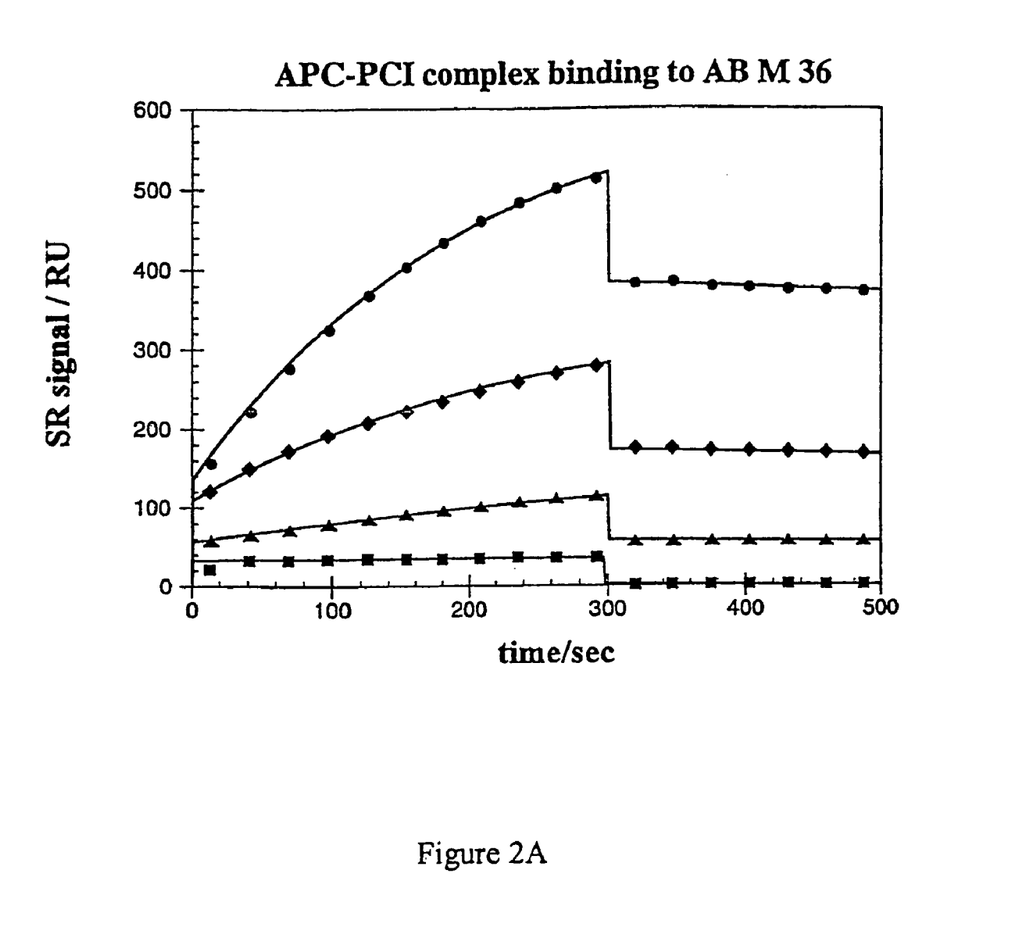
FIG. 2 shows measurements in real time of the interaction of APC:PCI complexes and cleaved PCI with the monoclonal antibody M36 using the surface plasmon resonance (SPR) technique. A) illustrates the interaction of APC:PCI complexes with M36, and the concentrations of the APC:PCI complexes were 17,6 nM (●), 8,8 nM (♦), 4,4 nM (▲) and 2,2 nM (▼). B) illustrates the interaction of cleaved PCI with M36, and the concentrations of cleaved PCI were 38,5 nM (●), 7,7 nM (●), 3,9 nM (▼), 1,9 nM (■) and 1,0 nM (♦). The lines were fitted to the experimental data, some of which are denoted by the symbols.
Figure 2B:
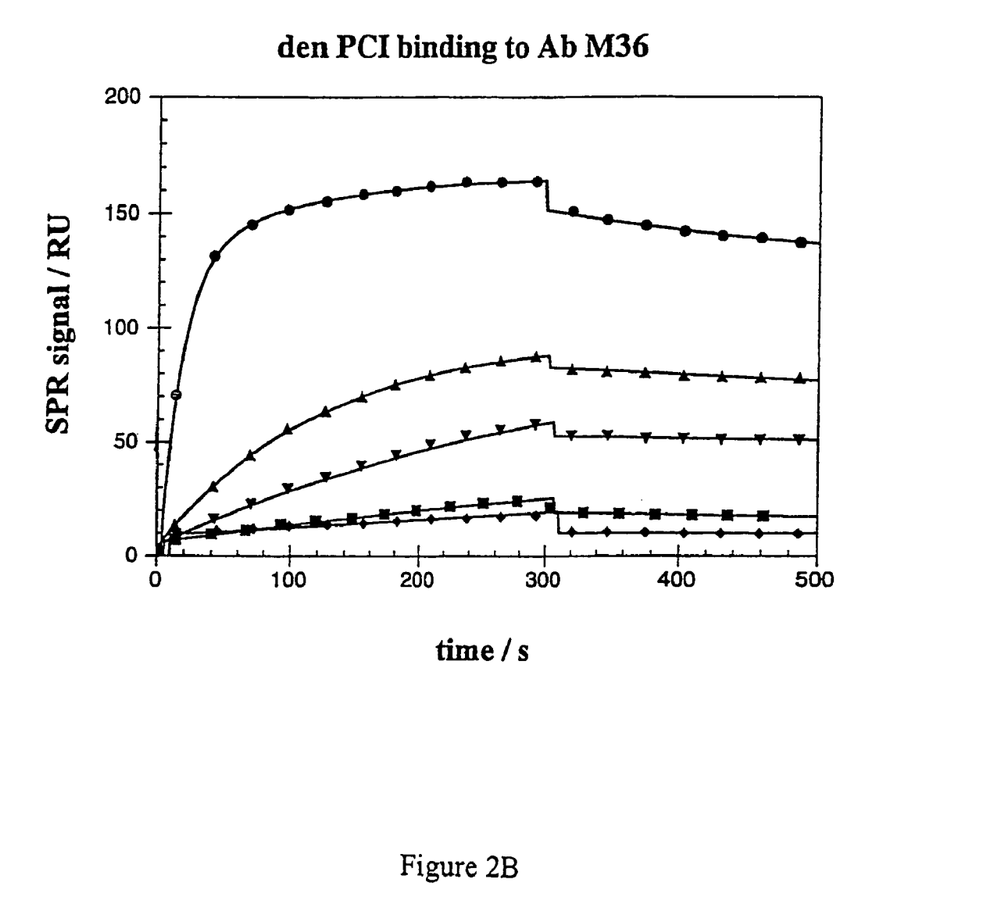

The dissociation constants of the antibody for its binding to PCI in complex with APC, cleaved PCI and native PCI, respectively, were measured with standard plasmon resonance technique. The dissociation constant, Kd, of M36 was $4 \times 10^{-10}$ M for PCI in complex with APC and $2 \times 10^{-10}$ M for the cleaved PCI, respectively, as is shown in FIG. 2. The value of Kd for the native PCI was too low, i.e. $\geq 10^{-5}$ M, to be determined accurately (not shown in FIG. 2). In summary, these results established that the selected monoclonal antibody M36 binds complexed PCI and cleaved PCI with very high affinity, but has very low, if any, affinity for native PCI.

As a tracer agent, a monoclonal antibody against protein C was used. This antibody, which was made by fusion of spleen cells with the myeloma cell line NS 1, is described by Ohlin, A. K. and Stenflo, J. (vide supra). Its epitope is in the calcium-binding N-terminal EGF-like domain of protein C, a domain exposed on both protein C and APC. Furthermore, this antibody binds to protein C and APC with high affinity, but the dissociation constant has not been quantitatively measured. The antibody binds to said epitope in a calcium-dependent manner, and it should be stated that no special requirements are made on this antibody, except that it should bind complexed APC with high affinity and can be labelled without any loss of affinity for the antigen. Among the protein C antibodies tested, this one worked best.

Collection of Blood:

Blood was collected in 5 ml siliconised glass vacuum tubes (Becton Dickinson) containing 0,5 ml of a 0,129 M trisodium citrate solution, to which benzamidine had been added to a concentration of 50 mM. Usually, the samples were centrifuged within 4 h after the blood was collected, and the plasma was either assayed immediately or frozen at $-70°$ C. The benzamidine greatly reduces the rate of complex formation between PCI and proteinases, such as kallikreine.

Performance of the Assay:

The catching antibody (M36) was biotinylated with a N-hydroxysuccinimide derivative of biotin (NHS-LC-Biotin®; Pierce) according to the instructions of the manufacturer. The biotinylated protein was dialysed against a 0,1 M sodium fosfate buffer (pH 7,0) containing 0,1% NaN$_3$, and it was typically stored at a concentration of 0,89 mg/ml at $+4°$ C.

To avoid the use of radioactivity and the need for enzyme conjugation of the tracer agent, i.e. HPC-4, a so-called DELPHIA® method was used. In said method, an Eu$^{3+}$ labelled tracer agent is utilised, and in this assay, the DELPHIA® Eu-labelling kit 1244-302 (Wallac) was used. The HPC-4 antibody can be heavily labelled with up to 80 Eu$^{3+}$ ions per antibody molecule without any loss of affinity for protein C. The tracer agent was stored as frozen aliquots at $-20°$ C. at a concentration of 0,043 mg/ml. Even if the DELPHIA® procedure was used in the present investigation, any commonly used means of labelling the tracer agent can probably be used.

Figure 3:
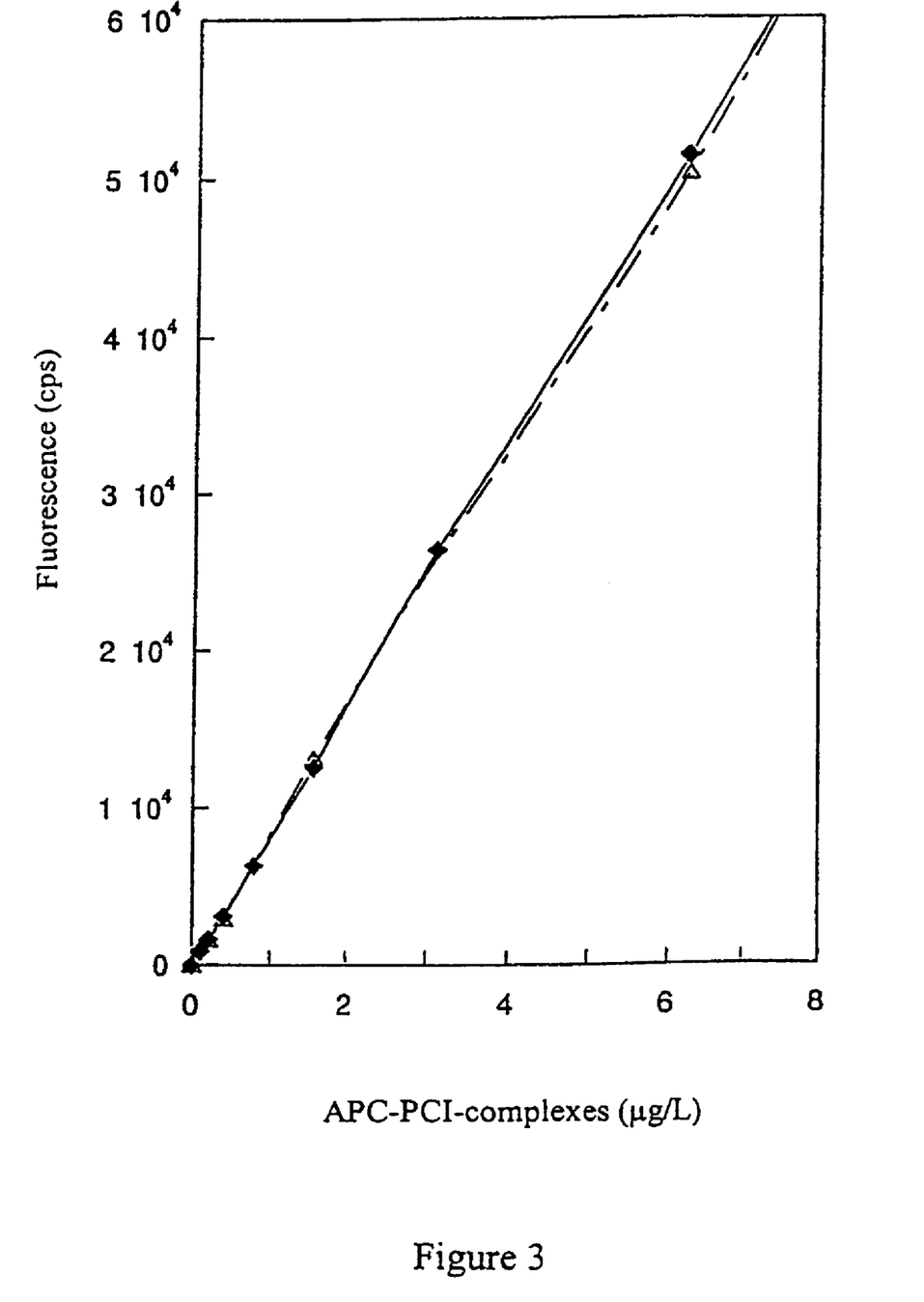

The biotinylated M36 antibody was diluted with assay buffer (Wallac assay buffer: 50 mM Tris-HCl, 0,9% NaCl, 0,05% NaN$_3$, 0,01% Tween 40, 0,05% bovine immunoglobulin, 0,5 μM DPTA and 20 μg/ml cherry red) to a concentration of 2 μg/ml prior to use. The samples were analysed in duplicate. 50 μl of buffer blank, standard samples, control samples, plasma blanks and plasma (patient) samples, respectively, were added to the wells of a 96 well microtiter plate (Sero-Wel, Bibby Sterlin Ltd.) followed by addition of 50 μl of the biotinylated M36 antibody to the standard, control and plasma samples, whereas 50 μl of assay buffer was added to the other samples. The plates were then put on a LKB, Wallac shaking device for 30 s followed by incubation at room temperature for 80 min. The entire sample was then transferred to a streptavidine coated plate (Microtitration strips, DELPHIA®, Wallac), after which the plate was shaken for 60 min on the shaking device, followed by washing in a plate washer (LKB, Wallac). 100 μl of the tracer agent solution was then added (20 ng/100 μl per well, diluted in assay buffer), followed by incubation on the shaking device for another 40 min at room temperature. After washing (Wallac wash fluid; Tris buffer, salt and Tween 20, pH 7,8), 200 μl of an enhancer solution (Wallac enhancement solution) was added to each well, and the plate was shaken on the shaking device for 10 min. Fluorescence was determined in an LKB-Wallac fluorimeter, and the APC:PCI complex formation was calculated by use of the program MultiCalc (Wallac) Here, it should be emphasized that the method according to the present invention gives a linear dose-response curve, as expected for a very high affinity antibody in a sandwich-type assay (FIG. 3).

In an alternative to the above procedure, the samples can be assayed directly on the streptavidine coated plate together with a biotinylated antibody, thereby avoiding the first incubation in a 96 well microtiter plate. In this manner, an even quicker procedure could be achieved without loss of performance. The time for the incubation with tracer can also be reduced. Such an alteration does not lead to any loss in the performance of the assay.

It should be noted that the standard curves are identical when made in buffer and in plasma, thus corroborating that the uncleaved inhibitor does not influence the assay. The signal given by APC:PCI complexes prior to the addition of standard has been subtracted (FIG. 3).

What is claimed is:

1. A monoclonal antibody suitable for monitoring the activity of systems involving a serpin protein C inhibitor, said monoclonal antibody having specific affinity for both
   (i) a complex between a serine proteinase and a serine proteinase inhibitor, and
   (ii) a cleaved an uncomplexed form of said serine proteinase inhibitor,
while having no specific affinity for said inhibitor in its uncleaved and active form of said serine proteinase inhibitor, wherein the serine protease inhibitor is a serpin.

2. A monoclonal antibody according to claim 1, wherein said monoclonal antibody is obtainable by immunisation of an animal with a mixture of
   (i) a complex between a serine proteinase and a serine proteinase inhibitor, and
   (ii) a cleaved and uncomplexed form of said serine proteinase inhibitor,
followed by screening for and isolation of said monoclonal antibody, wherein the serine proteinase inhibitor is a serpin.

3. A monoclonal antibody according to claim 2, wherein said animal is a mouse, preferably a Balb/c mouse.

4. A monoclonal antibody according to claim 1, wherein said serine proteinase is selected from the group consisting of activated protein C (APC), thrombin, coagulation factor $X_a$, trypsin, chymotrypsin, urokinase plasminogen activator (uPA), tissue type plasminogen activator (tPA), plasma kallikrein, factor $Xl_a$, human glandular kallikrein 1 (HGK1) and prostatic specific antigen (PSA).

5. A monoclonal antibody according to claim 1, wherein said inhibitor is protein C inhibitor (PCI) or $\alpha_1$-antitrypsin.

6. A method for preparation of a monoclonal antibody as defined in claim 1, wherein an animal is immunised with a mixture of
   i) a complex between a serine proteinase and a serine proteinase inhibitor, and
   ii) a cleaved form of said serine proteinase inhibitor, followed by screening for and isolation of said monoclonal antibody, wherein the serine proteinase inhibitor is a serpin.

7. A method for preparation of a monoclonal antibody according to claim 6, wherein said animal is a mouse, preferably a Balb/c mouse.

8. A method for monitoring the activity of systems involving protein C inhibitor, wherein a monoclonal antibody as defined in claim 1 is used in an immunoassay.

9. A method according to claim 8, wherein said immunoassay comprises a sandwich-type immunoassay.

10. A method according to claim 9, wherein said sandwich-type immunoassay is a technique comprising a tracer agent and said monoclonal antibody bound to a surface.

11. A method according to claim 10, wherein said tracer agent comprises an antibody having specific affinity for said serine proteinase or an epitope shared by said serine proteinase and said inhibitor.

12. A method according to claim 11, wherein said tracer agent is conjugated to a enzyme and/or labelled with a tracing substance.

13. A method according to claim 12, wherein said enzyme is an alkaline phosphatase, horse radish peroxidase or a $\beta$-galactosidase.

14. A method according to claim 13, wherein said tracing substance is $^{125}I$, $^{131}I$, $Eu^{3+}$ or $Sm^{3+}$.

15. A kit for qualitative or quantitative determination of the activity of systems involving protein C inhibitor comprising a monoclonal antibody according to claim 1.

16. A monoclonal antibody according to claim 2, wherein said serine proteinase is selected from the group consisting of activated protein C (APC), thrombin, coagulation factor $X_a$, trypsin, chymotrypsin, urokinase plasminogen activator (uPA), tissue type plasminogen activator (tPA), plasma kallikrein, factor $Xl_a$, human glandular kallikrein 1 (HGK1) and prostatic specific antigen (PSA).

17. A monoclonal antibody according to claim 2, wherein said inhibitor is protein C inhibitor (PCI) or $\alpha_1$-antitrypsin.

18. A method for preparation of a monoclonal antibody as defined in claim 2, wherein an animal is immunised with a mixture of
   i) a complex between a serine proteinase and a serine proteinase inhibitor, and
   ii) a cleaved form of said serine proteinase inhibitor, followed by screening for and isolation of said monoclonal antibody, wherein the serine proteinase inhibitor is a serpin.

19. A method for monitoring the activity of systems involving protein C inhibitor, wherein a monoclonal antibody as defined in claim 2 is used in an immunoassay.

20. A kit for qualitative or quantitative determination of the activity of systems involving protein C inhibitor comprising a monoclonal antibody according to claim 2.

* * * * *